United States Patent
Burton et al.

(10) Patent No.: US 7,722,090 B2
(45) Date of Patent: May 25, 2010

(54) METHOD AND APPARATUS FOR AN IMPROVED LUER FITTING CONNECTION

(75) Inventors: David G. Burton, Bloomington, IN (US); Scott K. Philhower, Bloomington, IN (US); Nicholas J. Ely, Ellettsville, IN (US)

(73) Assignees: Cook Incorporated, Bloomington, IN (US); Sabin Corporation, Bloomington, IN (US)

( * ) Notice: Subject to any disclaimer, the term of this patent is extended or adjusted under 35 U.S.C. 154(b) by 0 days.

(21) Appl. No.: 10/594,181

(22) PCT Filed: Mar. 24, 2005

(86) PCT No.: PCT/US2005/010037
§ 371 (c)(1),
(2), (4) Date: Nov. 27, 2007

(87) PCT Pub. No.: WO2005/097253
PCT Pub. Date: Oct. 20, 2005

(65) Prior Publication Data
US 2008/0193211 A1    Aug. 14, 2008

Related U.S. Application Data (60) Provisional application No. 60/556,559, filed on Mar. 26, 2004.

(51) Int. Cl.
*F16L 25/00* (2006.01)
(52) U.S. Cl. .................. 285/332; 403/342; 604/285
(58) Field of Classification Search ............. 403/109.2, 403/109.8, 287, 332–334, 305, 342; 285/332; 604/283
See application file for complete search history.

(56) References Cited

U.S. PATENT DOCUMENTS

| | | | |
|---|---|---|---|
| 3,747,632 A | | 7/1973 | Kok et al. |
| 4,735,441 A | * | 4/1988 | Stephens ............... 285/148.19 |
| 5,047,021 A | * | 9/1991 | Utterberg .................... 604/533 |
| 5,611,576 A | * | 3/1997 | Guala ........................... 285/38 |
| 5,620,427 A | * | 4/1997 | Werschmidt et al. ........ 604/535 |
| 5,651,776 A | | 7/1997 | Appling et al. |

(Continued)

FOREIGN PATENT DOCUMENTS

GB    735202    8/1955

(Continued)

*Primary Examiner*—Daniel P Stodola
*Assistant Examiner*—Joshua T Kennedy
(74) *Attorney, Agent, or Firm*—Woodard, Emhardt, Moriarty, McNett & Henry LLP (57) ABSTRACT

A method and apparatus for an improved luer fitting connector, in one embodiment, has a luer fitting connector including a male or female luer fitting member and a locking member. The locking member may have at least one of a skeletal handle, a finlike handle, a cavity grip, and an undulating grip. The luer fitting connector also may include a male or female luer fitting member having a conical restraining surface and a locking member having a plateau shaped protrusion. A method of assembly of luer fitting connector members may include providing a male or female luer fitting member having a conical restraining surface and providing a locking member having a plateau shaped protrusion. The method also may include mounting the locking member upon the male or female luer fitting member from the rear.

24 Claims, 5 Drawing Sheets

U.S. PATENT DOCUMENTS

| | | | |
|---|---|---|---|
| 5,702,374 A * | 12/1997 | Johnson | 604/533 |
| 5,830,195 A | 11/1998 | Peters et al. | |
| 5,919,169 A | 7/1999 | Grams et al. | |
| 5,931,597 A * | 8/1999 | Urbach | 403/134 |
| 5,984,373 A * | 11/1999 | Fitoussi et al. | 285/92 |
| 6,332,633 B1 | 12/2001 | Fitoussi et al. | |
| D454,637 S * | 3/2002 | Nestenborg | D24/130 |
| 6,565,550 B1 | 5/2003 | Klein et al. | |
| D483,869 S * | 12/2003 | Tran et al. | D24/129 |
| 6,673,059 B2 * | 1/2004 | Guala | 604/533 |
| 6,843,513 B2 * | 1/2005 | Guala | 285/332 |
| 6,893,056 B2 * | 5/2005 | Guala | 285/332.1 |
| D517,209 S * | 3/2006 | Burton et al. | D24/129 |
| 2002/0147429 A1 | 10/2002 | Cowan et al. | |
| 2004/0238776 A1 | 12/2004 | Peters et al. | |

FOREIGN PATENT DOCUMENTS

WO    WO 03/020361 3 A    3/2003

* cited by examiner

METHOD AND APPARATUS FOR AN IMPROVED LUER FITTING CONNECTION

REFERENCE TO RELATED APPLICATIONS

This application claims the benefit under 35 U.S.C. §365 of PCT/US2005/010037 filed Mar. 24, 2005 and under 35 U.S.C. §119(e) of U.S. provisional application Ser. No. 60/556,559, filed on Mar. 26, 2004, entitled "Method and Apparatus for an Improved Luer Fitting Connector," both of which are hereby incorporated by reference herein in their entireties.

FIELD OF THE INVENTION

The present invention relates generally to luer fitting connector assemblies. More particularly, the invention relates to a method and apparatus for an improved luer fitting connector having a locking member mounted upon a male luer fitting member.

BACKGROUND OF THE INVENTION

Luer fitting or luer lock connections are utilized in fluid flow conduits having medical or surgical applications. Typically, a male member has a slightly tapered body and is connected in fluid communication with a female member, which has a similarly tapered bore for receiving the male member. A coupling device or locking member commonly has an internally threaded collar. The locking member may further be mounted upon the body of the male member.

One purpose of the locking member is to prevent fluid leakage between the male and female members. Another purpose of the locking member is to maintain the connection between the male and female members.

However, luer fitting connectors are conventionally very small in size. Hence, with conventional designs, it can be difficult for an operator to maintain manual control of the luer fitting connector assembly, as well as rotate the locking member about the male and female members by hand.

Additionally, conventional luer fitting connector assemblies are often assembled by mounting the locking member onto the male member from the rear. The male member may have a restraining mechanism for restricting the longitudinal movement of the locking member after it is mounted upon the male member. In some conventional designs, the locking member has a plateau shaped protrusion for engagement with the restraining mechanism. In such assemblies, the locking member may be mounted upon the male member by forcing the plateau shaped protrusion over the restraining mechanism.

However, the male member exerts compression forces on the locking member as the plateau shaped protrusion is slid over the restraining mechanism from the rear. The compression forces applied tend to shorten the radial height of the plateau shaped protrusion. Yet, the plateau shaped protrusion must have enough elasticity to sufficiently limit the permanent plastic deformation, if any, that it experiences as a result of the applied compression forces such that the locking member cannot subsequently inadvertently "jump" back over the restraining mechanism. Thus, conventional designs disclose plateau shaped protrusions that experience compression forces that may lead to plastic deformation and the inadvertent separation of the locking and male luer fitting members after the locking member and the male luer fitting member are coupled together.

The present invention alleviates one or more of the shortcomings described above.

BRIEF SUMMARY

The present invention provides a method and apparatus that enhances the handling and control of a luer fitting connector assembly, as well as the rotation of the individual members with respect to each other. Additionally, the present invention may provide a method and apparatus that reduces the likelihood that the locking member will become inadvertently separated from the male luer fitting member after the locking member and the male luer fitting member are coupled together.

In one aspect of the present invention, an apparatus that enhances the handling and control of a luer fitting connector assembly is provided. The luer fitting connector assembly may include a male luer fitting member and a locking member having at least one of a cavity grip, a skeletal handle, a finlike handle, and an undulating grip.

In another aspect of the present invention, an apparatus that may reduce the likelihood that the locking member will become inadvertently separated from the male luer fitting member is provided. The luer fitting connector assembly may include a male luer fitting member and a locking member mounted upon the male luer fitting member. The male luer fitting member may have a restraining surface and the locking member may have a plateau shaped protrusion.

In yet another aspect of the present invention, a method of assembly of luer fitting members that may reduce the likelihood that the locking member will become inadvertently separated from the male luer fitting member is provided. The method may include providing a male luer fitting member having a conical restraining mechanism and providing a locking member having a plateau shaped protrusion. The method also may include mounting the locking member onto the male luer fitting member.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

The method and apparatus provided may beneficially enhance the handling and control of a luer fitting connector assembly, as well as enhance the rotation of the individual members with respect to each other. In the embodiments provided, a skeletal handle, a finlike handle, an undulating grip, or a cavity grip may be provided upon the locking member to enhance the manual control and operation of the luer fitting connector assembly. Additionally, a method and apparatus are provided that may reduce the magnitude of the compression forces that a locking member experiences as it is mounted upon a male luer fitting member. In the embodiments provided, the various members of the luer fitting connector assembly may be integrated in such a manner as to decrease the likelihood that the locking member will become inadvertently separated from the male luer fitting member upon which the locking member is mounted.

Figure 1:
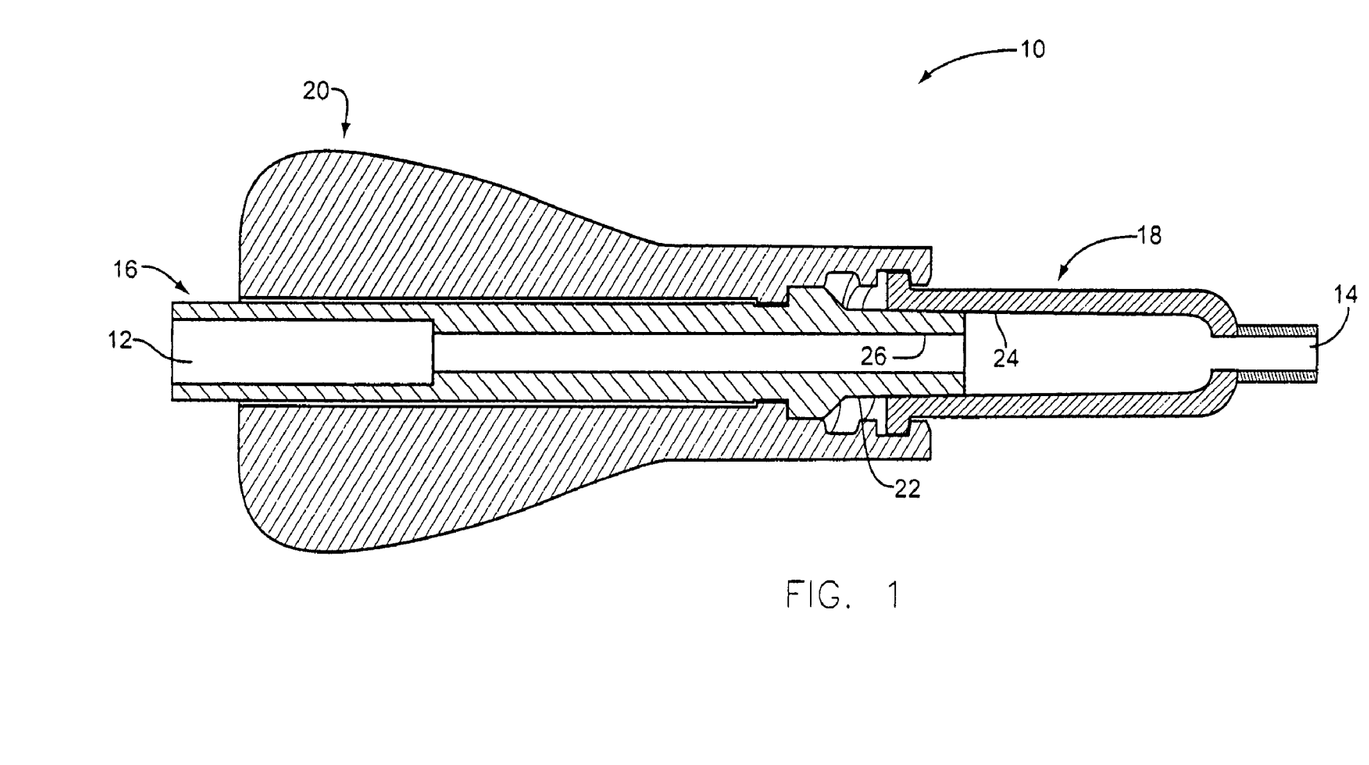
FIG. 1 is a longitudinal cross-sectional view of one embodiment of the apparatus of the present invention.

FIG. 1 illustrates a longitudinal cross-sectional view of a luer fitting connector assembly 10. The luer fitting connector assembly 10 may be utilized to connect a male fluid flow conduit 12 to a female fluid flow conduit 14. A male luer fitting member 16 may be inserted into a female luer fitting member 18 to connect the male fluid flow conduit 12 with the female fluid flow conduit 14. The connection between the male luer fitting member 16 and the female luer fitting member 18 may be maintained by the locking member 20. The locking member 20 illustrated may be rotably mounted upon and encircle the male luer fitting member 16. The luer fitting connector assembly 10 may have other configurations including those with fewer or additional components.

As illustrated in FIG. 1, the distal end of the male luer fitting member 16 may have a slightly tapered body 22. The proximal end of the female luer fitting member 18 may have a slightly tapered bore 24. The slightly tapered body 22 of the male luer fitting member 16 may be tapered at an angle corresponding to the taper angle of the slightly tapered bore 24 of the female luer fitting member 18. The exterior surface of the slightly tapered body 22 may uniformly mate with the slightly tapered bore 24. The result of the union between the slightly tapered body 22 and the slightly tapered bore 24 may be a tight seal or connection that prevents the leakage of fluid from the fluid flow conduit.

Additionally, the proximal end of the male luer fitting member 16 may have a cylindrical conduit 26. The cylindrical conduit 26 may have a tubular surface having a uniform cross-section orthogonal to longitudinal axis of the male fluid flow conduit 12. In one aspect, the cylindrical conduit 26 may have an interior diameter of approximately 2 mm.

Figure 2:
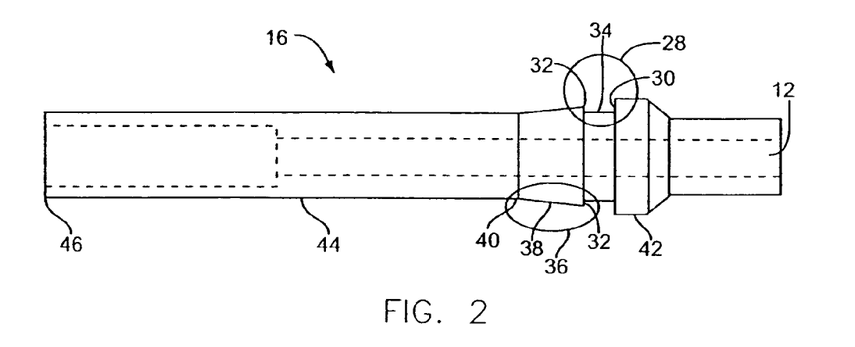
FIG. 2 is a longitudinal view of one embodiment of the male luer fitting member of the present invention.

FIG. 2 is an enlarged longitudinal view of the male luer fitting member 16. The male luer fitting member 16 may include a male fluid flow conduit 12, a rotary mount 28, a restraining surface 36, a distal tubular surface 42, and a proximal cylindrical body 44. The male luer fitting member 16 may have other configurations including those with fewer or additional components. In one aspect, the male luer fitting member 16 may have a longitudinal length of approximately 26 mm.

As illustrated in FIG. 2, the longitudinal cross-section of the rotary mount 28 may have a recess or indentation into the generally tubular exterior of the male luer fitting member 16. The rotary mount 28 may include a distal annular surface 30, a proximal annular surface 32, and a rotational surface 34.

The distal annular surface 30 may be a smooth surface approximately orthogonal to the longitudinal axis of the male fluid flow conduit 12. The proximal annular surface 32 may be a smooth surface approximately orthogonal to the longitudinal axis of the male fluid flow conduit 12. Additionally, both the distal annular surface 30 and the proximal annular surface 32 may be ring shaped.

The rotational surface 34 may be cylindrical in shape and may have a smooth exterior. The rotational surface 34 may be in communication with both the distal annular surface 30 and the proximal annular surface 32. The exterior of the rotational surface 34 may be approximately parallel to the longitudinal axis of the male fluid flow conduit 12. In one aspect, the longitudinal length of the rotational surface 34 may be approximately 1.6 mm and the diameter of the rotational surface 34 may be approximately 4.8 mm.

The angle of intersection between the rotational surface 34 and the distal annular surface 30 may be approximately 90 degrees. Additionally, the angle of intersection between the rotational surface 34 and the proximal annular surface 32 may be approximately 90 degrees. As shown in FIG. 2, the distal annular surface 30, the proximal annular surface 32, and the rotational surface 34 may form a generally u-shaped indentation or recess into the exterior of the male luer fitting member 16.

Moreover, the male luer fitting member 16 may include a restraining surface 36. The restraining surface 36 may have a tapered surface 38 and include the proximal annular surface 32. The tapered surface 38 may extend proximally from the proximal annular surface 32 to a washer end point 40. The tapered surface 38 may be generally smooth and conical in shape. The restraining surface 36 may have a cross-sectional area orthogonal to the longitudinal axis of the male fluid flow conduit 12 that decreases from the proximal annular surface 32 to the washer end point 40. In one aspect, the restraining surface 36 may have a diameter of approximately 5.3 mm at the proximal annular surface 32 and the tapered surface 38 may have a longitudinal length of approximately 3 mm.

The male luer fitting member 16 also may have a distal tubular surface 42. The distal tubular surface 42 may be generally smooth and may be cylindrical in shape. The exterior of the distal tubular surface 42 may be approximately parallel to the longitudinal axis of the male fluid flow conduit 12. The distal tubular surface 42 may engage the distal annular surface 30 at approximately a 90 degree angle. In one aspect, the tubular surface 42 may have a diameter of approximately 6.3 mm and a longitudinal length of approximately 2 mm.

Additionally, the male luer fitting member 16 may have a cylindrical body 44 extending from the washer end point 40 to a male member end point 46. The cylindrical body 44 may be tubular in shape. The exterior of the cylindrical body 44 may be generally smooth and approximately parallel to the longitudinal axis of the male fluid flow conduit 12. The cross-sectional area of the exterior of the cylindrical body 44 may be approximately constant.

Figure 3:
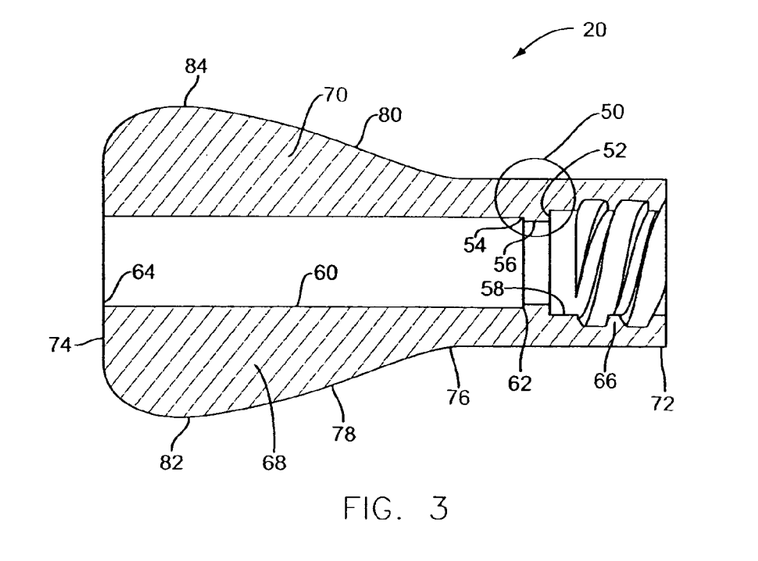
FIG. 3 is a longitudinal view of one embodiment of the locking member of the present invention.

FIG. 3 is a longitudinal cross-sectional view of the locking member 20. The locking member 20 may include a plateau shaped protrusion 50, a distal cylindrical surface 58, a proximal cylindrical surface 60, internal threads 66, a right handle 68, and a left handle 70. The locking member 20 may have other configurations including those with fewer or additional components. In one aspect, the locking member 20 may have a longitudinal length of approximately 34 mm.

As illustrated in FIG. 3, the longitudinal cross-section of the plateau shaped protrusion 50 may be an outward projection from the tubular interior of the locking member 20. The plateau shaped protrusion 50 may include a distal protrusion surface 52, a proximal protrusion surface 54, and a rotational protrusion surface 56.

The distal protrusion surface 52 may be a smooth surface approximately orthogonal to the longitudinal axis of the locking member 20. The proximal protrusion surface 54 may be a smooth surface approximately orthogonal to the longitudinal axis of the locking member 20. Both the distal protrusion surface 52 and the proximal protrusion surface 54 may be annular in shape.

The rotational protrusion surface 56 may be generally cylindrical in shape. The interior of the rotation protrusion surface 56 may be generally smooth and may be approximately parallel to the longitudinal axis of the locking member 20. The rotational protrusion surface 56 may be in communication with both the distal protrusion surface 52 and the proximal protrusion surface 54. In one aspect, the rotational protrusion surface 56 may have a longitudinal length of approximately 1.4 mm and may have an interior diameter of approximately 5.1 mm.

The angle of intersection between the rotational protrusion surface 56 and the distal protrusion surface 52 may be approximately 90 degrees. Additionally, the angle of intersection between the rotational protrusion surface 56 and the proximal protrusion surface 54 may be approximately 90 degrees. As shown in FIG. 3, the distal protrusion surface 52, the rotational surface 56, and the proximal protrusion surface 54 may form a generally u-shaped, or plateau shaped, protuberance from the interior surface of the locking member 20.

The locking member may include two interior cylindrical surfaces, a distal cylindrical surface 58 and a proximal cylindrical surface 60. The distal cylindrical surface 58 is generally smooth and is tubular in shape. The angle of intersection between the distal cylindrical surface 58 and the distal protrusion surface 52 may be approximately 90 degrees. In one aspect, the distal cylindrical surface 58 may have a longitudinal length of approximately 2 mm and may have an interior diameter that is approximately 7 mm.

The proximal cylindrical surface 60 may be generally smooth and slightly conical in shape. The proximal cylindrical surface 60 may extend from a protrusion edge 62 to a locking member end point 64. The proximal cylindrical surface 60 may intersect the proximal protrusion surface 54 at the protrusion edge 62. The angle of intersection between the proximal cylindrical surface 60 and the proximal protrusion surface 54 may be approximately 90 degrees. In one aspect, the proximal cylindrical surface 60 may have an interior diameter of approximately 5.7 mm at the protrusion edge 62 and may have an interior diameter of approximately 6.6 mm at the locking member end point 64.

As further illustrated in FIG. 3, the locking member 20 may include internal threads 66. The internal threads 66 may provide locking engagement between the locking member 20 and the female luer fitting member 18 (not shown).

Additionally, the locking member 20 may have a right handle 68 and a left handle 70. FIG. 3 shows the longitudinal cross-section of the right and left handles 68, 70. The longitudinal cross-section of both the right and left handle 68, 70 may have a shape similar to that of a dorsal fin of a fish.

The locking member 20 may have a distal surface 72, a proximal surface 74, and an intermediate point 76. In one aspect, the distance from the distal surface 72 to the intermediate point 76 may be approximately 14 mm.

From the intermediate point 76 to the proximal surface 74, the right and left handles 68, 70 may protrude radially from the exterior of the locking member 20. The longitudinal cross-sectional exterior surface 78 of the right handle 68 and the longitudinal cross-sectional exterior surface 80 of the left handle 70 may each be smooth and curved. In one aspect, the distance from the intermediate point 76 to the proximal surface 74 may be approximately 20 mm.

The magnitude of the outward extension of the right and left handles 68, 70 from the locking member 20 may extend to a right and left culmination point 82, 84, respectively. The longitudinal cross-sectional exterior surfaces 78, 80 at the proximal surface 74 of both the right and left handles 68, 70 may be perpendicular to the longitudinal axis of the locking member 20. From the right and left culmination points 82, 84 to the proximal surface 74, the longitudinal cross-sectional exterior surfaces 78, 80 of the right and left handles 68, 70 may each be curved along an arc of 90 degrees. In one aspect, the distance from the right culmination point 82 to the left culmination point 84 may be approximately 19 mm.

Figure 4:
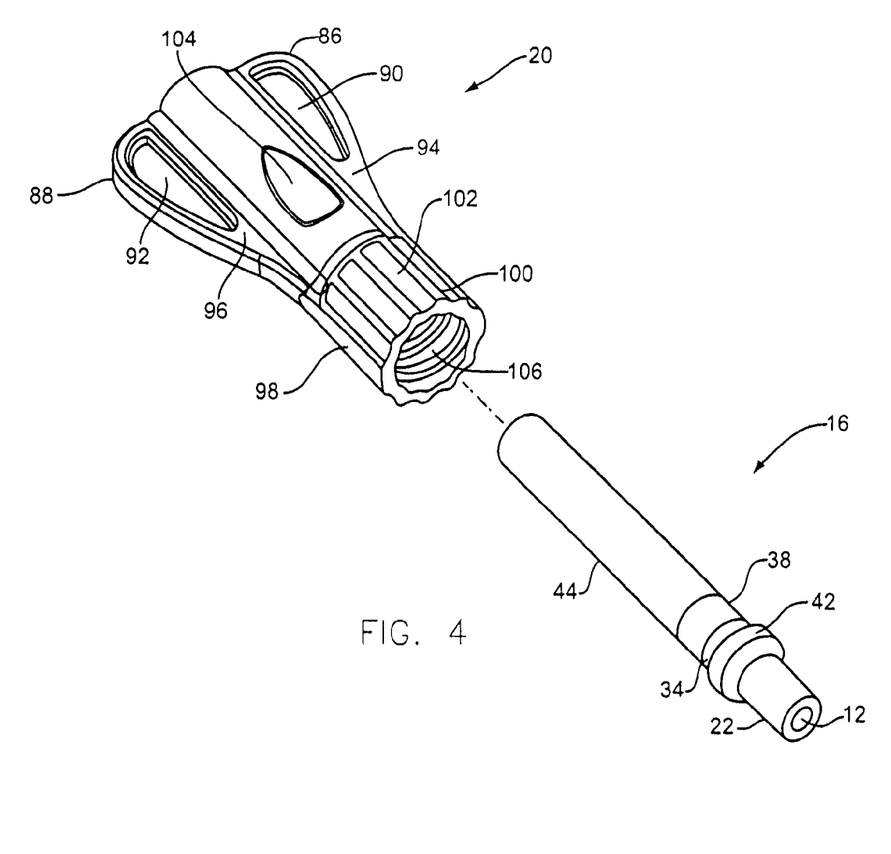
FIG. 4 is a perspective view of one embodiment of the locking member and the male luer fitting member of the present invention before assembly occurs.

FIG. 4 illustrates one embodiment of the locking member 20 and the male luer fitting member 16 before the locking member 20 is mounted upon the male luer fitting member 16 from the rear. The locking member 20 may include a right skeletal handle 86, a left skeletal handle 88, an undulating grip 98, a cavity grip 104, and an interior cavity 106. The male luer fitting member 16 may include a male fluid flow conduit 12, a slightly tapered body 22, a rotational surface 34, a tapered surface 38, a distal tubular surface 42, and a cylindrical body 44. The male luer fitting member 16 and locking member 20 may have other configurations including those with fewer or additional components.

The locking member 20 may have two skeletal handles, a right skeletal handle 86 and a left skeletal handle 88. The right skeletal handle 86 and the left skeletal handle 88 may each have an exterior shape that is similar to that of a dorsal fin of a fish. Additionally, the right skeletal handle 86 and the left skeletal handle 88 may each have a void or hollow opening 90, 92. Both the right void 90 and the left void 92 may have a shape that is similar to that of half of a pear.

The right skeletal handle 86 and the left skeletal handle 88 may each have a support section that supports each handle, respectively, during handling and turning operations. A right support section 94 and a left support section 96 may extend from the proximal end of an undulating grip 98 to the distal end of the right void 90 and the left void 92, respectively. In operation, the right skeletal handle 86 and the left skeletal handle 88 may each help an operator to handle and maintain control of, as well as turn, the locking member 20.

In one aspect, the locking member 20 may have an undulating grip 98. The undulating grip 98 may include a series of wave crests 100. A wave trough 102 may reside between the wave crests 100. Each wave crest 100 and wave trough 102 may extend approximately the entire longitudinal length of the undulating grip 98. In operation, the undulating grip 98 may help an operator to handle and maintain control of, as well as turn, the locking member 20.

The locking member 20 may have an exterior cavity grip 104. The exterior cavity grip 104 may be an indentation in the exterior surface of the locking member 20. The exterior cavity grip 104 may have a shape similar to that of a human thumbprint. In operation, the exterior cavity grip 104 may help an operator to handle and maintain control of, as well as turn, the locking member 20.

The locking member 20 may have a generally cylindrical interior cavity 106 for encompassing the male luer fitting member 16. The interior cavity 106 may run the entire length of the locking member 20.

As illustrated in FIG. 4, the distal end of the male luer fitting member 16 may have a slightly tapered body 22. The slightly tapered body 22 may be annular and have a conical exterior surface. The male fluid flow conduit 12 may run the entire length of the male luer fitting member 16.

The male luer fitting member 16 may have a distal tubular surface 42. The distal tubular surface 42 may have a smooth, cylindrical exterior. The male luer fitting member 16 may have a rotational surface 34 that also may have a smooth, cylindrical exterior. The outer diameter of the distal tubular surface 42 may be greater than the outer diameter of the rotational surface 34, as shown.

Additionally, the male luer fitting member 16 may have a tapered surface 38 that may have a smooth, conical exterior. The male luer fitting member 16 also may have a cylindrical body 44 located at one end. The cylindrical body 44 may have a tubular exterior and a uniform cross-section orthogonal to the longitudinal axis of the male fluid flow conduit 12.

FIG. 4 illustrates that the locking member 20 may be mounted onto the male luer fitting member 16 from the rear by slipping the male luer fitting member 16 into the interior cavity 106 of the locking member 20. As the male luer fitting member 16 slides over the locking member 20, eventually the plateau shaped protrusion 50 (not shown) of the locking member 20 may make contact with the tapered surface 38 of the male luer fitting member 16. By applying force in the longitudinal direction toward the distal end of the male luer fitting member 16, the plateau shaped protrusion 50 of the locking member 20 may slide over the tapered surface 38 of the restraining surface 36 (not shown). After sliding over the tapered surface 38, the plateau shaped protrusion 50 may be snapped into the u-shaped indentation of the rotary mount 28 (not shown).

The right skeletal handle 86 and left skeletal handle 88 may be utilized to turn the locking member 20 in either a clockwise or counter-clockwise manner with respect to the male luer fitting member 16. Additionally, either the undulating grip 98 or the exterior cavity grip 104 also may be utilized to turn the locking member 20 in either a clockwise or counter-clockwise manner with respect to the male luer fitting member 16.

Figure 5:
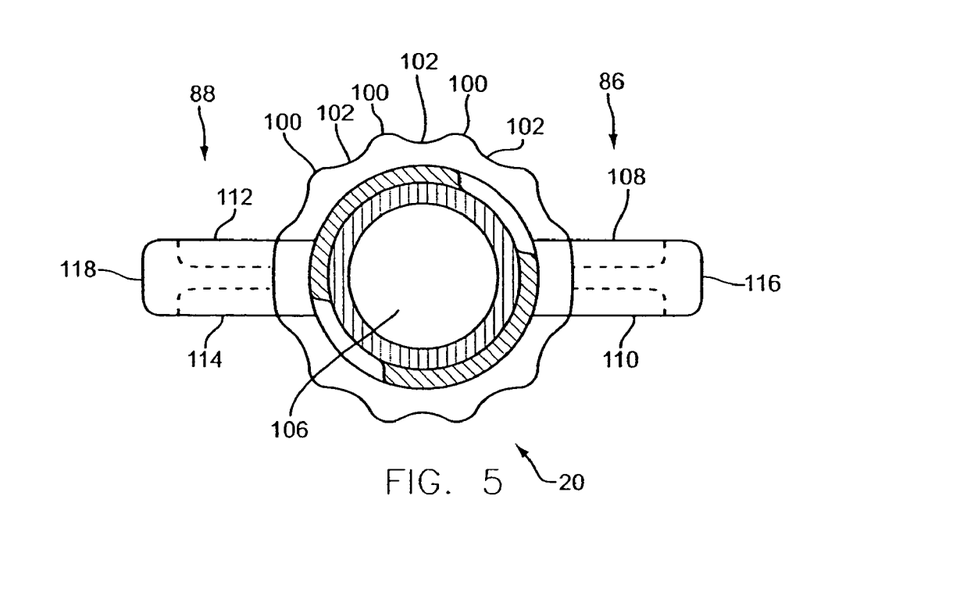
FIG. 5 is a perspective view of one embodiment of the locking member of the present invention.

FIG. 5 illustrates a different perspective view of the locking member 20. The locking member 20 may include a right skeletal handle 86, a left skeletal handle 88, wave crests 100, wave troughs 102, and an interior cylindrical cavity 106. The locking member 20 may have other configurations including those with fewer or additional components.

The right skeletal handle 86 may have a right top surface 108 and a right bottom surface 110. The left skeletal handle 88 may have a left top surface 112 and a left bottom surface 114. Each of the right and left top and bottom surfaces 108, 110, 112, and 114 may be generally smooth.

Additionally, the right skeletal handle 86 may have a right culmination surface 116 and the left skeletal handle 88 may have a left culmination surface 118. Both the right culmination surface 116 and the left culmination surface 118 may be generally smooth. The juxtaposition of the right top surface 108, right culmination surface 116, and right bottom surface 110 may form an approximately u-shaped exterior of the right skeletal handle 86. The juxtaposition of the left top surface 112, left culmination surface 118, and left bottom surface 114 may form an approximately u-shaped exterior of the left skeletal handle 88.

The locking member 20 may have a series of wave crests 100 and wave troughs 102. Each wave trough 102 may be curved and have a partially elliptical shape. Each wave crest 100 may be curved. In one aspect, there may be ten wave crests 100 and ten wave troughs 102. Additionally, the locking member 20 may have an interior cavity 106 that extends its entire length.

Figure 6:
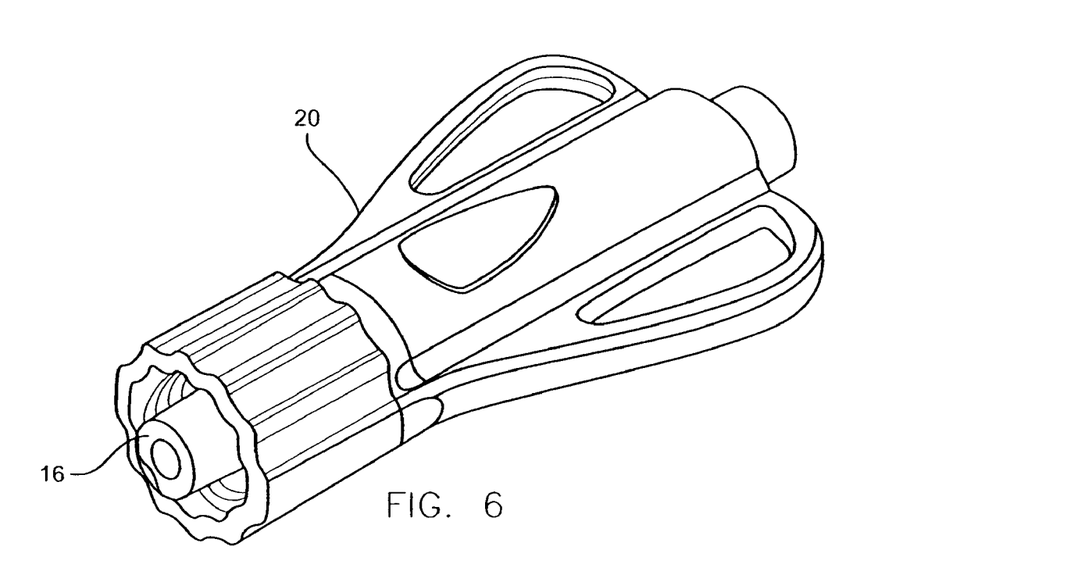
FIG. 6 is a perspective view of one embodiment of the present invention after the locking member is mounted upon the male luer fitting member.

FIG. 6 illustrates one aspect of the present invention after the locking member 20 is mounted upon the male luer fitting member 16. The male luer fitting member 16 and locking member 20 may have other configurations including those with fewer or additional components.

Figure 7:
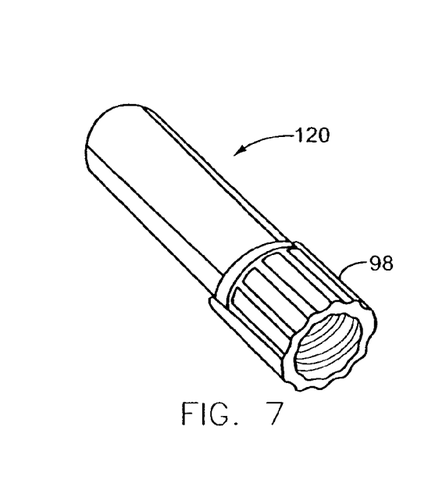
FIGS. 7-10 are alternate embodiments of the locking member.

FIG. 7 illustrates one alternate embodiment of a locking member 120. The locking member 120 may include an undulating grip 98 and no finlike handles (not shown), skeletal handles 86, 88 (not shown), or cavity grip 104 (not shown). The locking member 120 may have other configurations including those with fewer or additional components.

Figure 8:
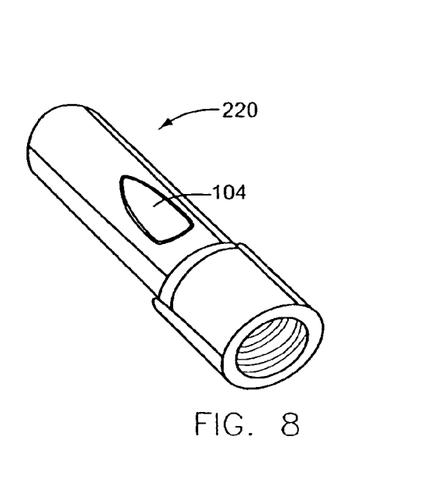

FIG. 8 illustrates another alternate embodiment of a locking member 220. The locking member 220 may include a cavity grip 104 and no finlike handles (not shown), skeletal handles 86, 88 (not shown), or undulating grip 98 (not shown). The locking member 220 may have other configurations including those with fewer or additional components.

Figure 9:
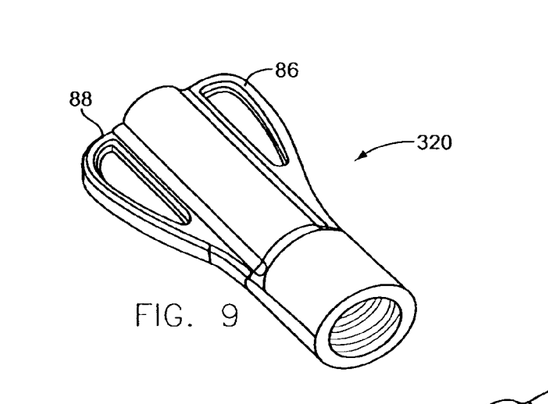

FIG. 9 illustrates another alternate embodiment of a locking member 320. The locking member 320 may include a pair of skeletal handles 86, 88 and no solid finlike handles (not shown), undulating grip 98 (not shown), or cavity grip 104 (not shown). The locking member 320 may have other configurations including those with fewer or additional components.

Figure 10:
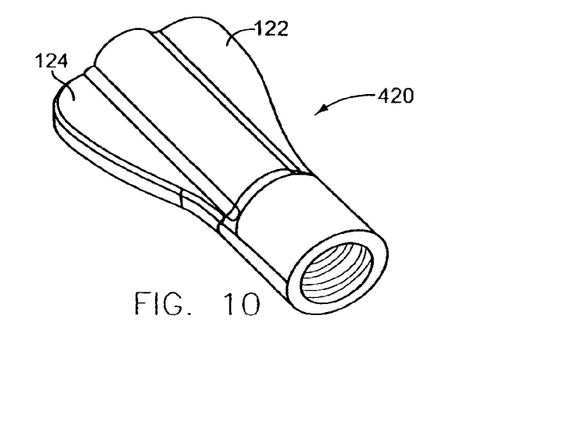

FIG. 10 illustrates another alternate embodiment of a locking member 420. The locking member 420 may include a pair of solid finlike handles 122, 124 and no skeletal handles 86, 88 (not shown), undulating grip 98 (not shown), or cavity grip 104 (not shown). The right and left finlike handles 122, 124 may have solid interior bodies without void spaces. The locking member 420 may have other configurations including those with fewer or additional components.

In operation, after the locking member 20 is mounted upon the male luer fitting member 16 and locks the male and female luer fitting members 16, 18 together, the distal protrusion surface 52 of the locking member 20 may mate with the distal annular surface 30 of the male luer fitting member 16 when the luer fitting assembly 10 experiences longitudinal stress tending to separate the male and female luer fitting members 16, 18. The union of the distal annular surface 30 with the distal protrusion surface 52 may effectuate a positive stop that maintains the male luer fitting member 16 and the female luer fitting member 18 in fluid communication.

Additionally, the restraining surface 36 may prevent the locking member 20 from substantially moving along the longitudinal axis of the male luer fitting member 16 after the locking member 20 is snapped onto the male luer fitting member 16. Any longitudinal force that would tend to lead to the inadvertent separation of the locking member 20 and the male luer fitting member 16 may cause the proximal protrusion surface 54 of the plateau shaped protrusion 50 to mate with the proximal annular surface 32 of the restraining surface 36. The union of the proximal annular surface 32 with the proximal protrusion surface 54 may effectuate a stop that maintains the plateau shaped protrusion 50 snapped into the rotary mount 28 and prevents the inadvertent separation of the locking member 20 from the male luer fitting member 16.

After the locking member 20 is mounted upon the male luer fitting member 16, turning the locking member in a clockwise manner may tighten the locking member 20 onto the female luer fitting member 18 and turning the locking member 20 in a counter-clockwise manner may loosen the connection between the locking member 20 and the female luer fitting member 18. In one aspect, there may be only clearance fits, as opposed to interference fits, between the possible contact surfaces of the locking member 20 and the male luer fitting member 16.

The present invention also discloses a method of assembly of luer fitting members. The method may prevent the inadvertent separation of locking member 20 from the male luer fitting member 16 after the two are coupled together. The method may include providing a male luer fitting member 16 and a locking member 20. The male luer fitting member 16 may comprise a restraining surface 36. The restraining surface 36 may have a rim approximately orthogonal to the longitudinal axis of the male fluid flow conduit 12 and may have a tapered surface 38.

The locking member 20 may have a plateau shaped protrusion 50 and a body that extends axially beyond at least a portion of the conical restraining surface 36 and toward the proximal end of the male luer fitting member 16, which is opposite the slightly tapered body 22. The locking member 20 may be mounted upon the male luer fitting member 16 from the rear of the male luer fitting member 16. The locking member 20 also may be rotably mounted upon the male luer fitting member 16.

The plateau shaped protrusion 50 of the locking member 20 may have a proximal protrusion surface 54 that is approximately orthogonal to the longitudinal axis of the locking member 20. The proximal protrusion surface 54 may uniformly mate with the proximal annular surface 32 of the rotary mount 28 of the male luer fitting member 16. In operation, the corresponding annular surfaces 54, 32 of the locking member 20 and male luer fitting member 16 mate when tension is applied that would tend to separate the locking member 20 and the male luer fitting members 16, thus preventing the inadvertent separation of the luer fitting assembly members. The method also reduces the compression forces experienced by the plateau shaped protrusion 50 as it slides over the restraining surface 36 and snaps into the rotary mount 28, resulting in the locking member 20 becoming coupled to the male luer fitting member 16. Moreover, the method may include fewer or additional acts that would be apparent to one skilled in the art from the above description of the various aspects of the apparatus.

Additionally, the method may enhance the handling and control of the members of a luer fitting connector assembly 10. The method may include providing a male luer fitting member 16 and a locking member 20. The method also may include rotably mounting the locking member 20 upon the male luer fitting member 16.

The method may include providing a locking member 20 comprising at least one of a skeletal handle 86, 88, an undulating grip 98, a cavity grip 104, and a finlike handle 122, 124. The finlike handle 122, 124 may have approximately the shape of a dorsal fin of a fish. The cavity grip 104 may have approximately the shape of a human thumbprint. The skeletal handle 86, 88, undulating grip 98, cavity grip 104, and finlike handle 122, 124 all enhance the handling and control of the members of a luer fitting connector assembly. Moreover, the method may include fewer or additional acts that would be apparent to one skilled in the art from the above description of the various aspects of the apparatus.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

It is therefore intended that the foregoing detailed description be regarded as illustrative rather than limiting, and that it be understood that it is the following claims, including all equivalents, that are intended to define the spirit and scope of this invention.

The invention claimed is:

1. A luer fitting connector assembly comprising:
 a male or female luer fitting member having a longitudinal axis and adapted for connection at a forward end thereof with a female or male luer fitting, respectively, the luer fitting member comprising a conical restraining surface, the conical restraining surface comprising a rim providing an end surface facing distally that is approximately orthogonal to said longitudinal axis, said luer fitting member having a rotary mount adjacent said rim defining a recess with a cylindrical rotational surface; and
 a one-piece locking member comprising a hollow central lumen, an annular, inwardly protruding plateau shaped protrusion providing an end surface facing proximally that is approximately orthogonal to a longitudinal axis of said lumen, and a body that extends axially beyond at least a portion of the conical restraining surface and toward the forward end of the luer fitting member;
 wherein the locking member can in assembly of the connector assembly be moved from a rearward end of the luer fitting member toward the forward end thereof, with said protrusion snapping over said conical restraining surface to position said rim end surface and said protrusion end surface to engage each other to provide a positive stop against separation of the locking member from the luer fitting member, and to position said protrusion in said recess such that said locking member is freely rotatable with respect to said rotational surface.

2. The luer fitting connector assembly of claim 1, wherein the locking member comprises a fin-shaped handle.

3. The luer fitting connector assembly of claim 2, wherein the fin-shaped handle radially extends outward from approximately one longitudinal end of the locking member.

4. The luer fitting connector assembly of claim 1, wherein the locking member comprises an undulating grip.

5. The luer fitting connector assembly of claim 4, wherein the undulating grip comprises ten waves.

6. The luer fitting connector assembly of claim 1, wherein the locking member comprises a skeletal handle.

7. The luer fitting connector assembly of claim 1, wherein the locking member comprises a cavity grip having an indentation approximating the shape of a human thumbprint.

8. The luer fitting connector assembly of claim 1, wherein the locking member comprises both a skeletal handle and an undulating grip.

9. The luer fitting connector assembly of claim 1, wherein the locking member comprises both a fin-shaped handle and an undulating grip.

10. The luer fitting connector assembly of claim 1 wherein the rim end surface uniformly mates with a corresponding annular surface of the plateau shaped protrusion.

11. The luer fitting connector assembly of claim 1 wherein the rim uniformly mates with a corresponding annular surface of the plateau shaped protrusion.

12. The luer fitting connector assembly of claim 1, wherein said luer fitting member is a male luer fitting member having an external surface adapted to contact the inside of a female luer fitting member when said male luer fitting member is assembled with said locking member.

13. The luer fitting connector assembly of claim 12, further comprising a female luer fitting member into which said forward end of said male luer fitting member is inserted, said female luer fitting member being connected to said locking member.

14. The luer fitting connector assembly of claim 1, wherein said rim is adapted to have a clearance fit in said locking member proximally of said protrusion end surface.

15. The luer fitting connector assembly of claim 1, wherein said locking member has a rotatable fit with respect to the luer fitting member when said rim is proximal of said protrusion.

16. The luer fitting connector assembly of claim 1, wherein said locking member extends along said luer fitting member on both sides of said conical restraining surface.

17. The luer fitting connector assembly of claim 1, wherein said luer fitting member includes a tubular surface forward of said conical restraining surface, and a non-orthogonal surface adjoining said tubular surface generally facing distally.

18. A method of assembling a luer fitting connector assembly comprising a locking member and a male or female luer fitting member, the method comprising:
   providing one of a male or female luer fitting members comprising a conical restraining surface, the conical restraining surface comprising a rim providing an end surface facing distally that is approximately orthogonal to the longitudinal axis of said one of the male or female luer fitting members, said luer fitting member having a rotary mount adjacent said rim defining a recess with a cylindrical rotational surface;
   providing a one-piece locking member comprising a hollow central lumen, an annular, inwardly protruding plateau shaped protrusion providing an end surface facing proximally that is approximately orthogonal to a longitudinal axis of said lumen, and a body that extends axially beyond at least a portion of the conical restraining surface and toward a forward end of said one of the male or female luer fitting member when the locking member is mounted upon said one of the male or female luer fitting members; and
   mounting the locking member upon said one of the male or female luer fitting members from a rear of said one of the male or female luer fitting members, with said protrusion snapping over said conical restraining surface so as to position said rim end surface and said protrusion end surface to engage each other to provide a positive stop against separation of the locking member from the luer fitting member and to position said protrusion in said recess such that said locking member is freely rotatable with respect to said rotational surface.

19. The method of assembling a luer fitting connector assembly of claim 18, wherein the rim end surface uniformly mates with a corresponding annular surface of the plateau shaped protrusion.

20. The method of assembling a luer fitting connector assembly of claim 18, wherein the rim uniformly mates with a corresponding annular surface of the plateau shaped protrusion.

21. The method of assembling a luer fitting connector assembly of claim 18, wherein the locking member comprises a fin-shaped handle.

22. The method of assembling a luer fitting connector assembly of claim 18, wherein the locking member comprises an undulating grip.

23. The method of assembling a luer fitting connector assembly of claim 18, wherein the locking member comprises a skeletal handle.

24. A luer fitting connector assembly comprising:
   a male or female luer fitting member having a longitudinal axis and adapted for connection at a forward end thereof with a female or male luer fitting, respectively, the luer fitting member comprising a conical restraining surface, the conical restraining surface comprising a rim providing a distally-facing surface, said luer fitting member having a rotary mount adjacent said rim defining a recess with a cylindrical rotational surface; and
   a one-piece locking member comprising a hollow central lumen, an annular, inwardly protruding plateau shaped protrusion providing a proximally-facing surface, and a body that extends axially beyond at least a portion of the conical restraining surface and toward the forward end of the luer fitting member;
   wherein the locking member can in assembly of the connector assembly be moved from a rearward end of the luer fitting member toward the forward end thereof, with said protrusion snapping over said conical restraining surface and positioned in said recess such that said locking member has a freely rotatable fit with respect to the rotational surface when said rim is proximal of said protrusion and wherein said proximally-facing surface is adapted in use of the connection to engage said distally-facing surface as a positive stop.

* * * * *